(12) United States Patent
Lindacher (10) Patent No.: US 7,080,906 B2
(45) Date of Patent: *Jul. 25, 2006

(54) TRANSLATING BIFOCAL WEAR MODALITY

(75) Inventor: Joseph Michael Lindacher, Suwanee, GA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/980,589

(22) Filed: Nov. 3, 2004

(65) Prior Publication Data

US 2005/0099595 A1    May 12, 2005

Related U.S. Application Data

(60) Provisional application No. 60/519,145, filed on Nov. 12, 2003.

(51) Int. Cl.
*G02C 7/06* (2006.01)

(52) U.S. Cl. ........................ 351/161; 351/177
(58) Field of Classification Search ................ 351/161, 351/164, 177
See application file for complete search history.

(56) References Cited

U.S. PATENT DOCUMENTS

| | | | | |
|---|---|---|---|---|
| 4,324,461 A | 4/1982 | Salvatori | ..................... | 351/160 |
| 4,537,479 A * | 8/1985 | Shinohara et al. | ........... | 351/169 |
| 4,573,775 A | 3/1986 | Bayshore | ..................... | 351/161 |
| 5,002,382 A | 3/1991 | Seidner | ......................... | 351/161 |
| 5,485,228 A | 1/1996 | Roffman et al. | ............ | 351/161 |
| 5,574,518 A | 11/1996 | Mercure | ...................... | 351/161 |
| 5,724,120 A | 3/1998 | Svochak et al. | ............ | 351/161 |
| 5,782,911 A | 7/1998 | Herrick | .......................... | 623/5 |
| 5,812,235 A | 9/1998 | Seidner et al. | .............. | 351/160 |
| 5,812,236 A | 9/1998 | Seidner et al. | .............. | 351/161 |
| 5,898,473 A | 4/1999 | Seidner et al. | .............. | 351/161 |
| 6,179,420 B1 | 1/2001 | Roffman et al. | ............ | 351/161 |
| 6,250,757 B1 | 6/2001 | Roffman et al. | ............ | 351/161 |
| 6,457,826 B1 | 10/2002 | Lett | ........................... | 351/161 |
| 2001/0033363 A1 | 10/2001 | Chateau et al. | ............. | 351/216 |
| 2003/0095231 A1 | 5/2003 | Ezekiel | ....................... | 351/161 |

FOREIGN PATENT DOCUMENTS

| | | |
|---|---|---|
| EP | 0 201 231 | 11/1986 |
| EP | 0 248 489 | 5/1987 |
| EP | 0 651 276 | 9/1999 |
| GB | 2 086 605 | 5/1982 |
| WO | WO 91/09336 | 6/1991 |
| WO | WO 01/53878 | 7/2001 |
| WO | WO 01/84216 | 11/2001 |
| WO | WO 02/064058 | 8/2002 |
| WO | WO 2004/072710 | 8/2004 |

OTHER PUBLICATIONS

International Search Report, Feb. 16, 2005.
Standard Search Report (European), Nov. 04, 1989.

* cited by examiner

*Primary Examiner*—Scott J. Sugarman
*Assistant Examiner*—Darryl J. Collins
(74) *Attorney, Agent, or Firm*—Jian Zhou (57) ABSTRACT

The invention discloses a pair of bifocal contact lenses: one lens for dominant eye and one lens for non-dominant eye. Both lenses have an optical zone divided into a superior zone and an inferior zone. The superior zone of the lens for dominant eye is for distance vision correction while the inferior zone is for near or intermediate vision correction. The superior zone of the lens for non-dominant eye is for distance or intermediate vision correction while the inferior zone is for near or intermediate vision correction.

25 Claims, 2 Drawing Sheets

TRANSLATING BIFOCAL WEAR MODALITY

This application claims priority to U.S. Provisional Application 60/519,145, filed Nov. 12, 2003, and is hereby incorporated by reference in its entirety.

The present invention relates to optics and, more specifically, to a pair of soft contact lenses.

BACKGROUND OF THE INVENTION

Contact lenses are widely used for many different types of vision deficiencies. These include defects such as near-sightedness and far-sightedness (myopia and hypermetropia, respectively), and defects in near range vision usually associated with aging (presbyopia). Presbyopia occurs as a person ages when the lens of eye begins lose its elasticity, eventually resulting in the eye losing the ability to focus on near objects. Such an individual will require additional vision correction for reading or working with a computer.

Some presbyopic persons have both near vision and far vision defects, requiring bifocal or multifocal lenses to properly correct their vision.

A typical single vision contact lens has a real or virtual focus, which is the point on which parallel rays of light focus when the lens is placed perpendicular to the parallel rays, and an optical axis, which is an imaginary line drawn from the focus to the center of the lens. The lens has a posterior surface that fits against the cornea and an opposite anterior surface. The optical zone, or zones, of the lens focus light to correct the eye's vision. In the case of a typical spherical lens, the optical zone has a single radius of curvature that is the distance from any point on the vision surface to a point on the optical axis referred to as the center of curvature.

A bifocal contact lens has at least two optical zones: a distance zone, for distance vision correction, and a near optical zone, for near vision correction (e.g., while reading).

While bifocal contact lens allow a person to improve their distance vision and near vision, the bifocal contact lens compromises intermediate vision correction, such as viewing a computer screen. The bifocal contact lens does not provide the needed correction.

Therefore, there is a need for a bifocal or multifocal wear modality that provides support not only to distance and near vision correction, but also intermediate vision correction.

SUMMARY OF THE INVENTION

The disadvantages of the prior art are overcome by the present invention that, in one aspect, is a pair of translating (segmented) multifocal contact lenses, a first contact lens for use in a wearer's dominant eye and a second contact lens for use in wearer's non-dominant eye. Each of the first and second lenses comprises an anterior surface and an opposite posterior surface. The anterior surface of each lens includes a vertical meridian and horizontal meridian, and a central optical zone. The central optical zone of each lens has a superior optical zone, an inferior optical zone, and an optical blending zone, wherein the optical blending zone has a surface that ensures a smooth surface transition from the superior optical zone to the inferior optical zone and that allows the superior and inferior optical zones independently of each other to be designed and optimized so that ghost images or blur from the superior and inferior optical zones is minimized or eliminated. The superior optical zone of the first lens is for distance vision correction and the inferior zone of the first lens is for intermediate or near vision correction. The superior optical zone of the second lens is for distance or intermediate vision correction and the inferior zone of the second lens is for intermediate or near vision correction. Preferably, the vision correction of the inferior zone of the first lens, whether intermediate or near correction, will be set by the wearer's subjective preference and predominant daily activities.

The invention also provides methods for manufacturing a pair of multifocal contact lenses described above for individuals requiring intermediate vision correction for extensive periods of time, such as computer users.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Unless defined otherwise, all technical and scientific terms used herein have the same meanings as commonly understood by one of ordinary skilled in the art to which this invention belongs. Generally, the nomenclature used herein and the laboratory procedures are well known and commonly employed in the art. Conventional methods are used for these procedures, such as those provided in the art and various general references.

The dominant eye determines the subjective visual line-of-sight of an individual.

Both the dominant eye and the non-dominant eye may require vision correction, and both eyes may need distance corrections, for example, myopia or hyperopia. Additionally, both eyes may require near vision correction for presbyopia as the person ages and the crystalline lens of each eye lose elasticity.

Figure 1A:
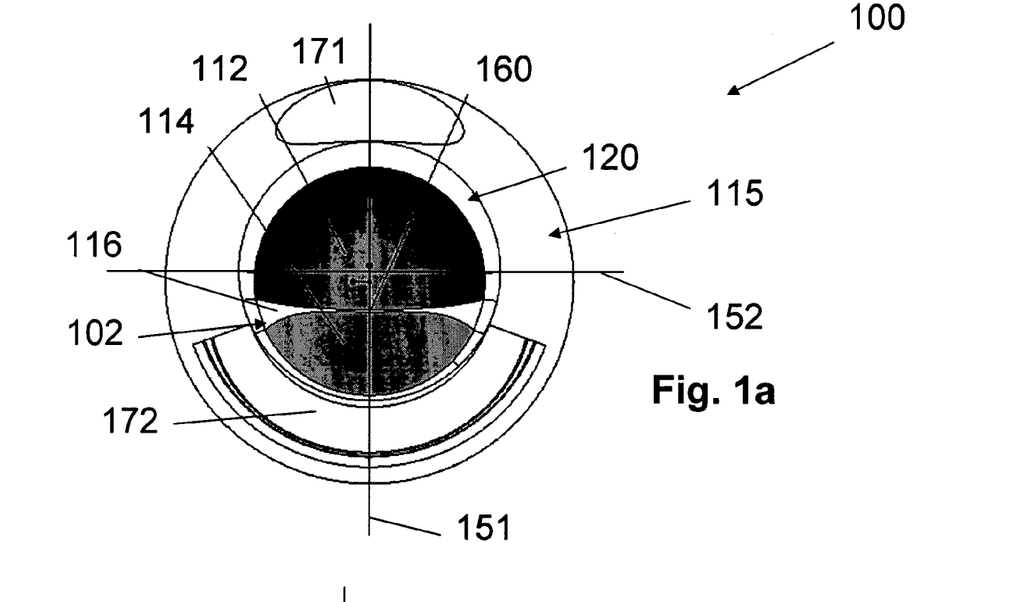
FIG. 1a is a front elevational view of a lens for a dominant eye according to a preferred embodiment of the invention.
Figure 1B:
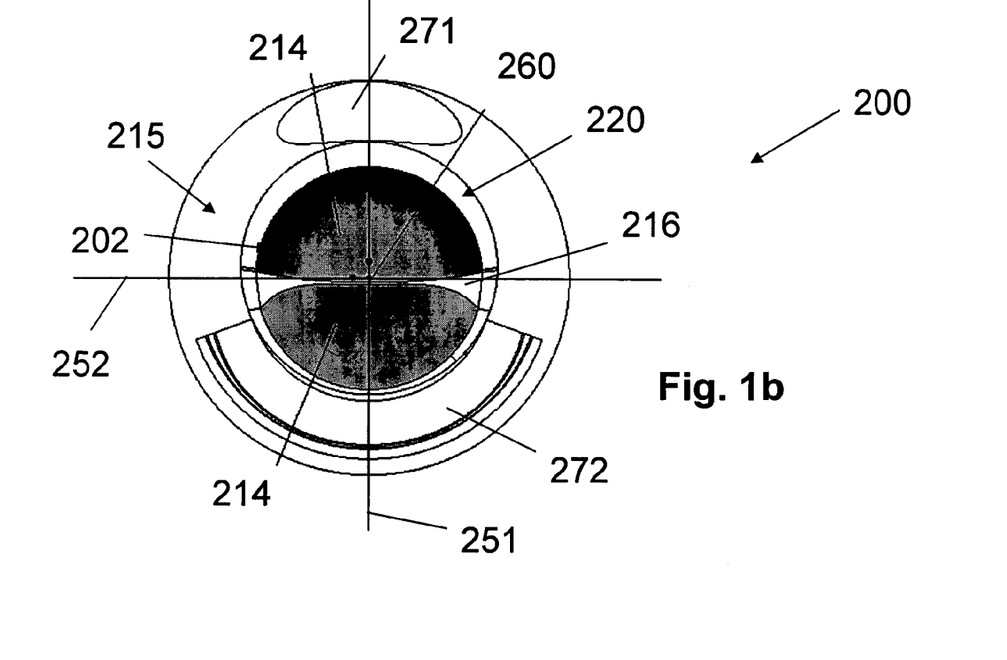
FIG. 1b is a front elevational view of an embodiment of a lens for a non-dominant eye according to a preferred embodiment of the invention.

FIGS. 1a and 1b illustrates schematically a pair of multifocal contact lens according to a preferred embodiment of the invention. The pair of lenses consists of a first lens 100 for a dominant eye (FIG. 1a) and a second lens 200 for the non-dominant eye (FIG. 1b).

As used herein, a "multifocal" contact lens can be a bifocal lens, a trifocal lens, a multifocal lens, or a progressive multifocal lens.

Each lens (100 or 200) in a pair of multifocal contact lenses of the invention has an anterior surface (or front curve) as shown in FIGS. 1a and 1b and an opposite posterior surface (or base curve) (not shown) which is rest on the cornea of the eye when worn by a user. The anterior surface of each lens includes a vertical meridian 151 or 251, a horizontal meridian 152 or 252, a central optical zone 102 or 202, a peripheral blending zone 120 or 220 extending outwardly from the central optical zone 102 or 202, and a peripheral (e.g., lenticular zone) 115 or 215 surrounding the blending zone 120 or 220.

"A lenticular" refers to a peripheral non-optical surface zone on the anterior surface of a contact lens between the optical zone and the edge. The primary function of the lenticular is to control the thickness of the lens edge and/or lens positional stability and/or to provide wearer's comfort.

It should be understood that the central optical zone is preferably concentric with the geometric center of the anterior surface, though the center of the central optical zone can be deviated from the geometric center of the anterior surface by up to 2 mm. The presence of a peripheral blending zone between the peripheral zone and the central optical zone is most preferably needed for enabling separate and independent designs of the central optical zone and the peripheral zone and for ensuring a continuous surface transition from the central optical zone to the peripheral zone. With a peripheral blending zone 120 or 220 between the central optical zone 102 or 202 and the peripheral zone 115 or 215, a contact lens can be produced to have flexion points and/or sharp edges at the junction between two zones being eliminated and thereby provide improved wearer's comfort. In addition, the peripheral blend zone 120 or 220 between the central optical zone 102 or 202 and the peripheral zone 115 or 215 can de-couple the optical features and the mechanical stabilization and translation features of the lens, thus preventing the introduction of prism into the optics. The peripheral blending zone 120 or 220 has a surface which ensures that the peripheral zone 115 or 215, the peripheral blending zone 120 or 220 and the central optical zone 102 or 202 are tangent to each other. The peripheral blending zone of the invention can be any surface described by a mathematical function, preferably a spline-based mathematical function, or made of different surface patches.

A "vertical meridian" refers to an imaginary line running vertically from the top, through the center, to the bottom of the anterior surface of a contact lens when said contact lens is maintained at a predetermined orientation on an eye. A "horizontal meridian" refers to an imaginary line running horizontally from the left side, through the center, to the right side of the anterior surface of a contact lens when said contact lens is maintained at a predetermined orientation on an eye. The horizontal and vertical meridians are perpendicular to each other.

"Surface patches" refer to combinations of curvatures and lines that are continuous in first derivative, preferably in second derivative, from each other.

It should be understood that the peripheral zone can be composed of one or more peripheral bands or regions which are patched together to form a continuous surface. Such peripheral zone can be a continuous surface defined by one or more mathematical functions, preferably by a spline-based mathematical function, or is made of several different surface patches.

The central optical zone 102 or 202 of each contact lens 100 or 200 comprises a superior optical zone 112 or 212, an inferior optical zone 114 or 214, and preferably an optical blend zone 116 or 216 between the superior and inferior optical zones (112 and 114, or 212 and 214).

The superior optical zone 112 or 212 of a lens covers the upper portion of the central optical zone. Preferably, the lower boundary line with the optical blending zone of the superior optical zone 112 or 212 is at or below a horizontal line passing through the center of the central optical zone 102 or 202 (the horizontal meridian or line parallel with the horizontal meridian) at least in its central portion (i.e., around the intersection point of the lower boundary line with the vertical meridian or with a line parallel to the vertical meridian and passing through the center of the central optical zone). More preferably, the lower boundary line with the optical blending zone 116 or 216 of the superior optical zone 112 or 212 is below a horizontal line passing through the center of the central optical zone 102.

The apex of superior optical zone 112 or 212 preferably coincides with the center of the central optical zone 102 or 202. The optical axis of the lens passes through the apex of the superior optical zone and the center of the optical zone of the posterior surface (base curve). The superior optical zone 112 or 212 can be defined by any mathematical function, for example, a spherical function, a conic function, a biconic function, Zernike polynomials, a spline-based mathematical function or combinations thereof.

The inferior optical zone 114 or 214 is located below the optical blending zone 116 or 216. The vertex center of the inferior optical zone 114 or 214 is preferably located on the vertical meridian or a line parallel to the vertical meridian and passing through the center of the central optical zone and on its boundary line with the optical blending zone. The inferior optical zone 114 or 214 can be defined by any mathematical function, for example, a spherical function, a conic function, a biconic function, Zernike polynomials, a spline-based mathematical function or combinations thereof.

For a segmented bifocal contact lens, such as contact lens (e.g., 100 as an illustrative non-limiting example), the images from both optical zones 112 and 114 on eye must be laterally coincident to minimize or eliminate ghost images. Ghost images are caused when the images from multiple optical zones on eye have lateral separation. The images from both zones will have an axial separation, on eye, typical of a bifocal lens. As embodied herein, the line passing through the vertex center of the inferior optical zone and the center of curvature at the vertex center of the inferior optical zone preferably intersects the line passing through the apex of the superior optical zone and the center of curvature at the apex of the posterior surface, wherein the intersection point is within 2 mm of the center of curvature at the apex of the base optical surface. Such optical zone may properly align the lateral images near the optical axis of the lens and controls image jump to the wearer.

In the preferred embodiment, the optimal alignment of the superior optical zone is controlled by rotating the inferior optical zone around the apex of the inferior optical zone. To properly align the lateral images, the line passing through the vertex center of the inferior optical zone and the center of curvature at the vertex center of the inferior optical zone should pass through the center of curvature of the (posterior) base curve surface. However, in the preferred embodiment, the asymmetrical stabilization and translation features of the lens require that the line passing through the vertex center of the inferior optical zone and the center of curvature at the vertex center of the inferior optical zone intersects the central axis of the posterior (or base curve) surface slightly displaced of the center of curvature.

The superior optical zone 112 or 212 is separated at least partially or completely by the optical blending zone 116 or 216 from the inferior optical zone 114 or 214. The distance between the superior and inferior optical zones along the vertical meridian or a line parallel to the vertical meridian and passing through the center of the central optical zone is preferably 0.5 mm or less, more preferably 0.2 mm or less, even more preferably 0.05 mm or less, most preferably 0.01 mm or less. Where the distance between the superior and inferior optical zones along the vertical meridian or a line parallel to the vertical meridian and passing through the center of the central optical zone is zero, the superior optical zone 112 or 212 and the inferior optical zone 114 or 214 are tangent at a common tangency point 160 or 260 which coincides with the vertex center of the inferior optical zone.

The optical blending zone 116 or 216 preferably has mirror symmetry with respect to a plane cutting through the vertical meridian or a line parallel to the vertical meridian and passing through the center of the central optical zone. The optical blending zone 116 or 216 has a surface that ensures a smooth surface transition from the superior optical zone 112 or 212 to the inferior optical zone 114 or 214. The optical blend zone 116 or 216 preferably contains a localized curvature (optical power) much higher than either of the superior and inferior optical zones so that light will be refracted away from the Macular region of the eye. The blending between the superior zone 112 or 212 and inferior zone 114 or 214 of a bifocal contact lens design optimizes the imaging properties for the wearer's gazes.

In general, the surface sag difference between the superior and inferior optical zones prevents a smooth surface transition. Therefore, in the preferred embodiment, the magnitude of the curvature of the blend zone surface will be much greater than the curvature of the optical zones. In the preferred embodiment, the optical blend zone 116 or 216 surface will have an inflection predominately in the horizontal direction.

As further shown in FIGS. 1a and 1b, the optical blending zone 116 or 216 horizontally extends between the superior optical zone 112 or 212 and inferior optical zone 114 or 214, from the center point 160 or 260 located on the vertical meridian (or a line parallel to the vertical meridian and passing through the center of the central optical zone) to the periphery of the contact lens 100 or 200. The optical blending zone 116 or 216 also outwardly flares from the vertical meridian towards the periphery of the contact lens 100 or 200. The width of the optical blending zone 116 or 216 increases toward the periphery of the central optical zone to provide controlled curvature, controlled optical power, and a smooth surface transition to the optical zone-to-lenticular zone blend. When the pupil is subtended by the optical blend zone 116 or 216, the problems associated with ghost images and blur may occur. The optical blending zone and optical zones configuration of present invention minimizes these problems.

The blend zone 116 or 216 can be formed by creating two surfaces that are properly aligned for optimal vision and separated by a distance of 1.5 mm or less from the vertex center of the inferior optical zone to the apex of the superior optical zone. The inferior optical zone 114 or 214 will be rotated around the vertex center of the inferior optical zone 114 or 214 to laterally align the images from both the superior and inferior optical zones. The boundaries, common to the blend zone 116 or 216, of the two properly designed, aligned superior and inferior optical zones preferably flare at the periphery in order to maintain a relatively smooth curvature across the blend zone 116 or 216. The width of the optical blending zone will be on the order of 0.1 mm or less at the center (along the vertical meridian or a line parallel to the vertical meridian and passing through the center of the central optical zone) and 1 mm at the periphery. In the preferred embodiment, the bounding curves can be defined by splines or $4^{th}$ order or higher mathematical functions and projected onto the surface.

For example, the central optical zone on the anterior surface of a bifocal contact lens of the invention can be designed as follows. A first optical surface is designed to provide a desired optical power for intermediate or distance vision correction. The central axis of the first optical surface coincides with the central axis of the posterior surface. A first projecting curve on a plane (xy-plane) perpendicular to the central axis of the posterior surface is projected onto the first optical surface to form the boundary line of the superior optical zone with the optical blending zone.

Then, a second optical surface is designed to provide a desired optical power for intermediate or near vision correction. A second projecting curve on a plane (xy-plane) perpendicular to the central axis of the second optical surface is projected onto the second optical surface to form the boundary line of the inferior optical zone with the optical blending zone. The designed inferior optical zone is placed in the central optical zone of the anterior surface by positioning the vertex center of the designed inferior optical zone at a desired point along the vertical meridian (or a line parallel to the vertical meridian and passing through the center of the central optical zone) below the superior optical zone. Preferably, the designed inferior optical zone is placed in the central optical zone of the anterior surface in a way such that the designed inferior optical zone and the first optical surface (the portion below the boundary line of the first optical zone with the optical blending zone) are tangent to each other at the vertex center of the designed inferior optical zone. The positioned inferior optical zone is then rotated around the vertex center of the inferior optical zone to properly align the inferior optical zone in relative to the superior optical zone.

The first and second projecting curves, independently of each other, can be a sixth order mathematical function (eqs. 1 and 2)

$$\text{Upper\_Cut}(t) := \delta + T1 \cdot OZD^2 \cdot (t-0.5)^2 + T2 \cdot OZD^4 \cdot (t-0.5)^4 + T3 \cdot OZD^6 \cdot (t-0.5)^6 \quad (1)$$

$$\text{Lower\_Cut}(t) := -\delta + B1 \cdot OZD^2 \cdot (t-0.5)^2 + B2 \cdot OZD^4 \cdot (t-0.5)^4 + B3 \cdot OZD^6 \cdot (t-0.5)^6 \quad (2)$$

wherein: $\delta$ is the central gap between the superior and inferior optical zones (i.e., along the vertical meridian);

OZD is the optical zone diameter;

T1 is the $2^{nd}$ order coefficient for the primary (superior) zone;

T2 is the 4th order coefficient for the primary zone;

T3 is the 6th order coefficient for the primary zone;

B1 is the $2^{nd}$ order coefficient for the secondary (inferior) zone;

B2 is the 4th order coefficient for the secondary zone;

B3 is the 6th order coefficient for the secondary zone; and t is the parametric parameter [0:1]

Figure 2:
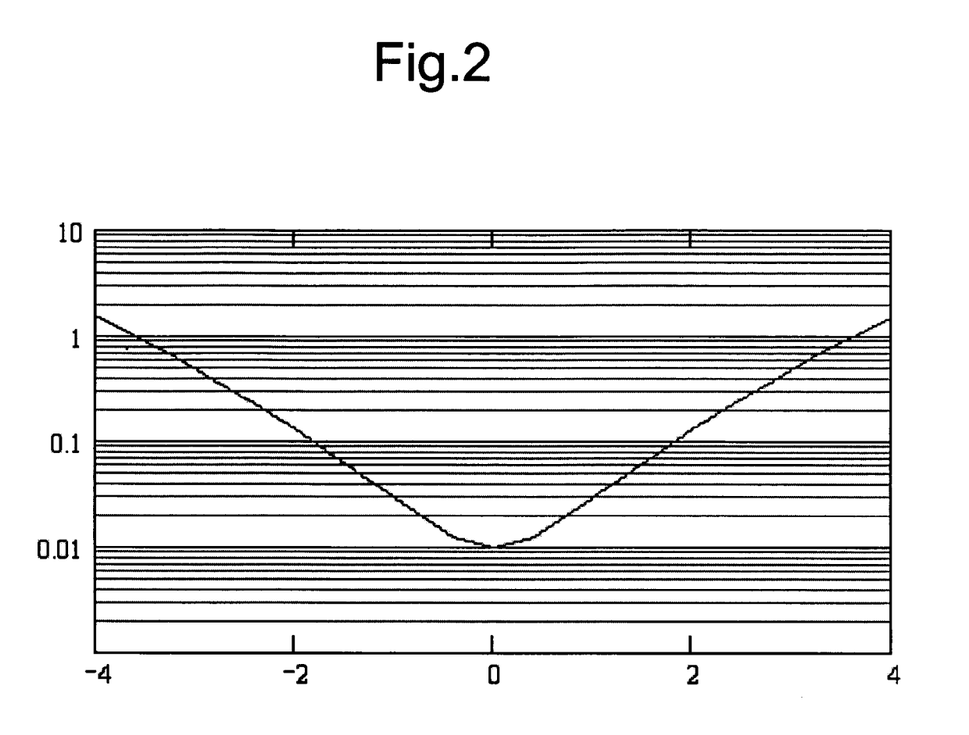
FIG. 2 schematically illustrates gap profile (distance between the first and second optical zones as function of distance to the vertical meridian of the anterior surface of a contact lens according to a preferred embodiment.

FIG. 2 schematically illustrates a gap profile, y-axis, (distance between the superior and inferior optical zones) as function of distance (x-axis) to the vertical meridian of the anterior surface. The boundary line of the superior optical zone with the optical blending zone is derived from a projecting curve defined by eq. 1, wherein $\delta$ is 0.005 mm, OZD is 8 mm, T1 is 0.02, T2 is 0.0001, and T3 is 0.00001. The boundary line of the inferior optical zone with the optical blending zone is derived from a projecting curve defined by eq. 2, wherein δ is 0.005 mm, OZD is 8 mm, B1 is 0.005, B2 is −0.003, and B3 is −0.0001.

In accordance with the present invention, one of a pair of multifocal lenses has a superior optical zone for distance vision correction and an inferior optical zone for intermediate or near vision correction. The other one of the pair of multifocal lenses has a superior optical zone for distance or intermediate vision correction and an inferior optical zone for intermediate or near vision correction.

An optical power for distance vision correction typically is equal to a manifest corrective refractive power. As used herein "manifest refraction" means a user's subjective best correction for an eye. The "manifest corrective refractive power" means a refractive power required for achieving a user's subjective best correction for an eye.

An optical power for intermediate or near vision correction typically equal to the sum of a manifest corrective refractive power and an added optical power with an ADD value. The ADD value generally provides an optimal vision correction for intermediate or near vision. The ADD value depends on the degree of Presbyopia and typically ranges from 1 Diopter to 3 Diopters.

The ADD value needed for reading at close distance is greater than the ADD value needed for reading a computer screen at an intermediate distance. It is recommended that the ADD value for the intermediate vision correction zone to be between 25% and 75% of the ADD value for the near vision correction zone, so the optimal vision for the intermediate distance can be achieved. For example, for the ADD value of 1 diopter for the near zone, the ADD value for the intermediate zone should be between 0.25 and 0.75 diopter; for the ADD value of 2 diopter for the near zone, the ADD value for the intermediate zone should be between 1 and 0.5 diopter; for the ADD value of 3 diopter for the near zone, the ADD value for the intermediate zone should be between 1.5 and 0.75 diopter. It is understood that the recommended ADD value typically depends on the age of a person.

Where the inferior optical zone of a contact lens of the invention is an optical zone for near vision correction, it is desirable that the size of the inferior zone is smaller than that of the superior zone as shown in FIG. 1a. The size ratio of the superior optical zone to the inferior optical zone is about 1.6 or larger. At least 65% of the lower boundary line of the superior optical zone 112 with the optical blending zone 116 is below a horizontal line passing through the center of the central optical zone 102 (the horizontal meridian or line parallel with the horizontal meridian), at least in its central portion (i.e., around the intersection point of the lower boundary line with the vertical meridian or with a line parallel to the vertical meridian and passing through the center of the central optical zone). The distance from the apex of the superior optical zone 112 to the intersection point of the vertical meridian or a line which is parallel to the vertical meridian and passes through the center of the central optical zone with the lower boundary line of the superior optical zone 112 with the optical blending zone 116 is from 0.5 to 1.5 mm, preferably from 0.75 to 1.25 mm, more preferably from 0.9 to 1.1 mm.

Where the inferior optical zone of a contact lens of the invention is an optical zone for intermediate vision correction, it is desirable that the size of the inferior zone is equal to or slightly smaller than that of the superior zone as shown in FIG. 1b. The size ratio of the superior optical zone to the inferior optical zone is about 1.5 or smaller. The distance from the apex of the superior optical zone 212 to the intersection point of the vertical meridian or a line which is parallel to the vertical meridian and passes through the center of the central optical zone with the lower boundary line of the superior optical zone 212 with the optical blending zone 216 is less than about 0.8 mm, preferably less than 0.5 mm, more preferably less than 0.3 mm.

The ADD value, which the inferior zone of a lens for the dominant eye can have, depends on a wearer's predominant activities. Generally, it is recommended the use of the dominant eye for the wearer's predominant non-distance viewing activities. For example, if the wearer is a computer user and his predominant non-distance activity is viewing a computer screen at an intermediate distance, then the dominant eye should be used for activities in the intermediate distance, i.e., the inferior zone of the lens for the dominant eye should be used for intermediate distance activities, such as viewing a computer screen. The inferior zone of the lens for the non-dominant eye will then be used for near distance activities, such as reading.

Alternatively, if the wearer is a truck driver, who typically views distance in primary gaze or views a map at a near distance in down-gaze, then the dominant eye should be used for activities in the near distance in down-gaze, i.e., the inferior zone of the lens for the dominant eye should be used for near distance activities, such as map reading, and the inferior zone of the lens for the non-dominant eye should be used for intermediate distance activities, as shown in FIGS. 1a and 1b.

FIGS. 1a and 1b illustrate a preferred embodiment of the invention. The superior zones 102 and 202 for both lenses 100 and 200 provides correction for the distance vision, but the ADD value for the inferior zones 106 and 206 are different. The lens 100 for the dominant eye has an inferior optical zone 106 for near vision correction (ADD=+3.0D), whereas the lens 200 for the non-dominant eye has an inferior optical zone for intermediate vision correction (ADD=+1.5D).

In a preferred embodiment, the superior optical zone of a lens of the invention includes a vertically oriented coma-like aberration that is more myopic in the inferior sections of the superior optical zone. The vertically oriented coma-like aberration will create an intermediate vision zone.

A "coma-like wavefront aberration" refers to a wavefront aberration which is, or is an equivalent of, a wavefront aberration described by any one of third order, fifth order, seventh order Zernike coma-like terms, and combinations thereof in the proposed OSA Standard (Optical Society of America) Zernike Polynomials.

A table of the proposed OSA Standard (Optical Society of America) Zernike Polynomials up to $7^{th}$ order is displayed below (More information on Zernike polynomials is available on http://color.eri.harvard.edu/standardization/standards TOPS4.pdf).

Table of Zernike Polynomials in Polar Coordinates up to $7^{th}$ order (36 terms)

| j | n | m | $Z_n^m (\rho, \theta)$ |
|---|---|---|---|
| 0 | 0 | 0 | 1 |
| 1 | 1 | −1 | $2\rho \sin\theta$ |
| 2 | 1 | 1 | $2\rho \cos\theta$ |
| 3 | 2 | −2 | $\sqrt{6}\rho^2 \sin 2\theta$ |
| 4 | 2 | 0 | $\sqrt{3}(2\rho^2 - 1)$ |
| 5 | 2 | 2 | $\sqrt{6}\rho^2 \cos 2\theta$ |
| 6 | 3 | −3 | $\sqrt{8}\rho^3 \sin 3\theta$ |
| 7 | 3 | −1 | $\sqrt{8}(3\rho^3 - 2\rho) \sin\theta$ |
| 8 | 3 | 1 | $\sqrt{8}(3\rho^3 - 2\rho) \cos\theta$ |
| 9 | 3 | 3 | $\sqrt{8}\rho^3 \cos 3\theta$ |

-continued

Table of Zernike Polynomials in Polar Coordinates up to 7th order (36 terms)

| j | n | m | $Z_n^m (\rho, \theta)$ |
|---|---|---|---|
| 10 | 4 | −4 | $\sqrt{10}\rho^4 \sin 4\theta$ |
| 11 | 4 | −2 | $\sqrt{10}(4\rho^4 − 3\rho^2) \sin 2\theta$ |
| 12 | 4 | 0 | $\sqrt{5}(6\rho^4 − 6\rho^2 + 1)$ |
| 13 | 4 | 2 | $\sqrt{10}(4\rho^4 − 3\rho^2) \cos 2\theta$ |
| 14 | 4 | 4 | $\sqrt{10}\rho^4 \cos 4\theta$ |
| 15 | 5 | −5 | $\sqrt{12}\rho^5 \sin 5\theta$ |
| 16 | 5 | −3 | $\sqrt{12}(5\rho^5 − 4\rho^3) \sin 3\theta$ |
| 17 | 5 | −1 | $\sqrt{12}(10\rho^5 − 12\rho^3 + 3\rho) \sin \theta$ |
| 18 | 5 | 1 | $\sqrt{12}(10\rho^5 − 12\rho^3 + 3\rho) \cos \theta$ |
| 19 | 5 | 3 | $\sqrt{12}(5\rho^5 − 4\rho^3) \cos 3\theta$ |
| 20 | 5 | 5 | $\sqrt{12}\rho^5 \cos 5\theta$ |
| 21 | 6 | −6 | $\sqrt{14}\rho^6 \sin 6\theta$ |
| 22 | 6 | −4 | $\sqrt{14}(6\rho^6 − 5\rho^4) \sin 4\theta$ |
| 23 | 6 | −2 | $\sqrt{14}(15\rho^6 − 20\rho^4 + 6\rho^2) \sin 2\theta$ |
| 24 | 6 | 0 | $\sqrt{7}(20\rho^6 − 30\rho^4 + 12\rho^2 − 1)$ |
| 25 | 6 | 2 | $\sqrt{14}(15\rho^6 − 20\rho^4 + 6\rho^2) \cos 2\theta$ |
| 26 | 6 | 4 | $\sqrt{14}(6\rho^6 − 5\rho^4) \cos 4\theta$ |
| 27 | 6 | 6 | $\sqrt{14}\rho^6 \cos 6\theta$ |
| 28 | 7 | −7 | $4 \rho^7 \sin 7\theta$ |
| 29 | 7 | −5 | $4 (7\rho^7 − 6\rho^5) \sin 5\theta$ |
| 30 | 7 | −3 | $4 (21\rho^7 − 30\rho^5 + 10\rho^3) \sin 3\theta$ |
| 31 | 7 | −1 | $4 (35\rho^7 − 60\rho^5 + 30\rho^3 − 4\rho) \sin \theta$ |
| 32 | 7 | 1 | $4 (35\rho^7 − 60\rho^5 + 30\rho^3 − 4\rho) \cos \theta$ |
| 33 | 7 | 3 | $4 (21\rho^7 − 30\rho^5 + 10\rho^3) \cos 3\theta$ |
| 34 | 7 | 5 | $4 (7\rho^7 − 6\rho^5) \cos 5\theta$ |
| 35 | 7 | 7 | $4 \rho^7 \cos 7\theta$ |

A vertically oriented coma-like aberration is wavefront aberration which is, or is an equivalent of, a wavefront aberration described by at least one of the third order coma-like Zernike term Z7, the fifth order coma-like Zernike term Z17, the seventh order coma-like term Z31 and combinations thereof.

In another preferred embodiment, the central optical zone of a lens of the invention can have a progressive power zone between the superior and inferior zones.

In another preferred embodiment, the central optical zones 12,14 can alternately include a spherical aberration that is less myopic at the periphery of each zone. At a distance of 3 mm from the center of any optical zone, the magnitude of spherical aberration will be, on the order of, 1 diopter of all lenses of the series. Typically, a presbyopic eye exhibits 1 diopter or more of spherical aberration that is more myopic in the periphery, for a 6 mm pupil. The actually spherical aberration created in the lens will also be a function of spherical aberration coupling, to the eye, for that lens design and lens material.

In general, the narrow optical blend zone 116 or 216 in the central region will be smoothed over by the manufacturing processes. In the periphery, the magnitude of the optical power will be significantly different than the optical region. In the preferred embodiment, the optical blend zone 116 or 216 to the lenticular region 115 or 215 may be asymmetrical to optimize blending in this region. Further, the curvature at the ends of the optical blend zone 116 or 216 can refract off-axis light to the retina such that the light provides a visual cue as to the orientation of the lens 100 or 200 for the wearer.

An contact lens of the invention preferably comprises one or more orientation/stabilization features (171, 172, 271, 272). Any suitable orientation/stabilization features can be used in the invention. Exemplary orientation/stabilization features include, without limitation, a prism ballast or the like that uses a varying thickness profile to control the lens orientation; a faceted surface in which parts of the lens geometry is removed to control the lens orientation; a ridge feature which orients the lens by interacting with the eyelid, double slab-off features which have a top slab-off zone 171 or 271 and a bottom slab-off zone zones to maintain the lens orientation on the eye as well as a visual cue on the lenses so that a wearer can insert the lenses in the proper orientation; non-prism ballast features in the peripheral zone of the lens, disclosed in a co-pending U.S. patent application Ser. No. 60/401,736 filed on Aug. 6, 2002, entitled "Contact lenses" (herein incorporated by reference in its entirety); and the like.

Preferably, the orientation/stabilization features of a contact lens of invention comprises on the anterior surface of the lens a ramped ridge zone 172 or 272, which is described in a copending U.S. patent application No. 60/398,485 filed on Jul. 24, 2002, entitled "Translating Contact Lens Having A Ramped Ridge", herein incorporated by reference in its entirety. The ramped ridge zone is disposed below the second optical zone and includes an upper edge, a lower ramped edge, a latitudinal ridge that extends outwardly from the anterior surface, and a ramp that extends downwardly from the lower ramped edge and has a curvature or slope that provides a varying degree of interaction between the ramped ridge zone and the lower eyelid depending on where the lower eyelid strikes the ramped ridge zone. The lower eyelid of the eye is engaged with at least some portion of the ramped ridge zone at all times. Such ramped ridge zone can provide wearer's comfort and also is capable of controlling contact lens position on an eye in primary gaze and/or translating amount across the eye when the eye changes from gazing at an object at a distance to gazing at an object at an intermediate distance or at a nearby object. Preferably, when transforming the design of an optimized optical model lens into a mechanical lens design, some common features of a family of contact lenses can be incorporated.

More preferably, the orientation/stabilization features of a contact lens of invention comprises non-prism ballast features in the peripheral zone of the lens, disclosed in a co-pending U.S. patent application Ser. Nos. 60/401,736 (incorporated herein by reference in its entirety). It was discovered that, when a contact lens has in the peripheral zone (non-optical zone surrounding the optical zone) a lens thickness profile characterized by having a thickness which increases progressively from the top of the lens downwardly along each of the vertical meridian and lines parallel to the vertical meridian until reaching a maximum value at a position between the optical zone and the edge zone and then decreases to the edge of the edge zone, such contact lens can be maintained at a predetermined orientation on an eye. Like a conventional lens ballast, such orientation feature works by weighing the lens at the bottom, causing it to come to an equilibrium position on the eye. With such orientation feature, the optical zone of the anterior surface can be designed independently that can provide an optimal visual performance.

In particular, the orientation/stabilization features of a contact lens of invention comprises do not provide an prism optical distortion and can maintain the lens in a predetermined orientation on an eye, such as those disclosed in a copending U.S. patent application Ser. No. 60/472,365 filed May 21, 2003 entitled "Contact Lenses" (herein incorporated by reference in its entirety). The anterior surface of a contact lens further includes a peripheral zone, an edge zone, a first blending zone extending outwardly from the central optical zone to the peripheral zone and providing a continuous transition from the central optical zone to the peripheral zone, a second blending zone extending outwardly from the peripheral zone to the edge zone and providing a continuous transition from the peripheral zone to the edge zone. The anterior surface has a mirror symmetry with respect to a vertical meridian plane and is continuous at least in first derivative. The contact lens is weighed at its lower half portion by varying lens thickness within the peripheral zone and second blending zone to cause it to come to an equilibrium position on the eye and has a lens thickness profile characterized by that the lens thickness, in a sector bounded by two sector-bounding semi-meridians at about 35 degrees or larger relative to the lower portion of the vertical meridian and by a portion of the edge included between the two sector-bounding semi-meridians, increases gradually from the inner boundary of the peripheral zone along each semi-meridian until reaching a lens thickness maximum and then decreases. In alternative preferred embodiments, the lens thickness profile is further characterized by that: (1) the lens thickness, along the upper portion of the vertical meridian, of the contact lens in the peripheral zone remains substantially constant or increases gradually from the outer boundary of the peripheral zone to the inner boundary of the peripheral zone in a manner that the difference between the values of lens thickness at two intersection points of the upper portion of the vertical meridian with the outer and inner boundaries of the peripheral zone is less than 50%, preferably by less than 30%, more preferably less than 15%; and/or (2) the lens thickness, along the lower portion of the vertical meridian, of the contact lens in the peripheral zone increases gradually from the inner boundary of the peripheral zone to the outer boundary of the peripheral zone in a manner that the difference between the values of lens thickness at two intersection points of the lower portion of the vertical meridian with the inner and outer boundaries of the peripheral zone is from about 15% to about 65%.

A "outer boundary", in reference to a zone other than a central optical zone on the anterior surface of a contact lens, refers to one of two peripheral boundaries of that zone which is further away from the geometric center of the anterior surface.

An "inner boundary", in reference to a zone other than a central optical zone on the anterior surface of a contact lens, refers to one of two peripheral boundaries of that zone which is closer to the geometric center of the anterior surface.

A "semi-meridian" refers to an imaginary line running radially from the geometric center of the anterior surface of a contact lens to the edge of the contact lens.

The "upper portion of the vertical meridian" refers to one half vertical meridian that is above the geometric center of the anterior surface of a contact lens, when said lens is maintained at a predetermined orientation on an eye.

The "lower portion of the vertical meridian" refers to one half vertical meridian that is below the geometric center of the anterior surface of a contact lens, when said lens is maintained at a predetermined orientation on an eye.

A "continuous transition", in reference to two or more zones, means that these zones are continuous at least in first derivative, preferably in second derivative.

A "vertical meridian plane" refers to a plane that cuts through the optical axis of a contact lens and a vertical meridian on the anterior surface of the contact lens.

A "sector", in reference to the anterior surface of a contact lens, means an area bounded by two sector-bounding semi-meridians at an equal angle relative to the lower portion of the vertical meridian and by a portion of the edge included between the two sector-bounding semi-meridians. The edge included between the two sector-bounding semi-meridians is the sum of a first portion of the edge between one of the two semi-meridians and the lower portion of the vertical meridian and a second portion of the edge between the other semi-meridian and the lower portion of the vertical meridian.

Two "sector-bounding semi-meridians" refer to two semi-meridians which divides the anterior surface into two sectors.

"Lens thickness" refers to a shortest distance from a point on the anterior surface to the posterior surface of a contact lens.

A "percentage of difference between two values of lens thickness" is obtained by first subtracting the smaller value from the larger value and then dividing the subtracting result with the larger value and finally multiplying it with 100.

A "blending zone" refers to a non-optical zone located between two zones and providing a continuous transition between these two zones.

The presence of a first blending zone can allow to separately and independently design the central optical zone and the peripheral zone, so as to ensure a continuous transition from the central optical zone to the peripheral zone. With a first blending zone between the central optical zone and the peripheral zone, a contact lens can be produced to have flexion points and/or sharp boundaries at the junction between two zones being eliminated and thereby provide improved wearer's comfort. In addition, the first blending zone between the central optical zone and the peripheral zone can de-couple the optical features and the mechanical stabilization and translation features of the lens, thus preventing the introduction of prism into the optics. The first blending zone has a surface that ensures that the peripheral zone, the first blending zone and the central optical zone are tangent to each other. The blending zone of the invention can be any surface described by a mathematical function, preferably a spline-based mathematical function, or made of different tangent surface patches.

"Tangent surface patches" refer to combinations of surfaces with curvatures that are continuous in first derivative, preferably in second derivative, from each other.

The peripheral zone can be composed of one or more peripheral bands or regions which are patched together to form a continuous surface. It is discovered that, when a contact lens has in the peripheral zone and the second blending zone a lens thickness profile as described above, such contact lens can be maintained effectively at a predetermined orientation on an eye. Like a conventional lens ballast, the orientation feature of the invention works by weighing the lens at its lower half portion, causing it to come to an equilibrium position on the eye. With such orientation feature, the optical zone of the anterior surface can be designed independently to provide an optimal visual performance.

The following is a description of a use scenario for a pair of the bifocal lenses according to the invention. A wearer, who is a computer user with a dominant left eye, has an eye examination from an eye doctor and a pair of bifocal contact lenses are made for his use. The predominant non-distance viewing activity for the wearer is viewing a computer screen.

The superior zones of the both lenses have the prescription for correcting the distance vision. The inferior zone for the non-dominant eye (right eye) has the correction for the near vision, and the inferior zone for the dominant eye (left eye) has the correction for intermediate vision.

If the user needs to read a manual, he places the manual on his desk and views through the inferior zone of both lenses for reading. He adjusts his vision by focusing the text in the manual through his non-dominant eye, since reading the manual is a non-predominant viewing activity. The selection of which eye to rely requires certain training, but the user will acquire it easily.

Contact lenses of the invention can be either hard or soft lenses. Soft contact lenses of the invention are preferably made from a soft contact lens material, such as a silicon or fluorine-containing hydro-gel or HEMA. It will be understood that any lens material can be used in the production of a contact lens of the invention.

A contact lens of the invention can be designed using any known, suitable optical design system. Exemplary optical computer aided design systems for designing an optical model lens includes, but are not limited to ZEMAX (Focus Software, Inc.). Preferably, the optical design will be performed using ZEMAX (Focus Software, Inc.). The design of the optical model lens can be transformed by, for example, a mechanical computer aided design (CAD) system, into a set of mechanical parameters for making a physical lens. Any know suitable mechanical CAD system can be used in the invention. The design of an optical model lens may be translated back and forth between the optical CAD and mechanical CAD systems using a translation format which allows a receiving system, either optical CAD or mechanical CAD, to construct NURBs (non-uniform rational B-splines) or Bézier surfaces of an intended design. Exemplary translation formats include, but are not limited to, VDA (verband der automobilindustrie) and IGES (Initial Graphics Exchange Specification). By using such translation formats, overall surface of lenses can be in a continuous form that facilitates the production of lenses having radial asymmetrical shapes. Bezier and NURBs surface are particular advantageous for a lens having a plurality of zones including optical zone and non-optical zones because multiple zones can be blended, analyzed and optimized. More preferably, the mechanical CAD system is capable of representing precisely and mathematically high order surfaces. An example of such mechanical CAD system is Pro/Engineer from Parametric Technology. When transforming the design of an optical model lens into a set of mechanical parameters, common feature parameters of a family of contact lenses can be incorporated in the lens designing process. Examples of such parameters include shrinkage, non-optical edge zone and its curvature, center thickness, range of optical power, and the like.

A contact lens of the invention may be produced by any convenient manufacturing means, including, for example, a computer-controllable manufacturing device, molding or the like. A "computer controllable manufacturing device" refers to a device that can be controlled by a computer system and that is capable of producing directly a contact lens or optical tools for producing a contact lens. Any known, suitable computer controllable manufacturing device can be used in the invention. Exemplary computer controllable manufacturing devices includes, but are not limited to, lathes, grinding and milling machines, molding equipment, and lasers. Preferably, a computer controllable manufacturing device is a two-axis lathe with a 45° piezo cutter or a lathe apparatus disclosed by Durazo and Morgan in U.S. Pat. No. 6,122,999 (herein incorporated by reference in its entirety), or is a numerically controlled lathe, for example, such as Optoform® ultra-precision lathes (models 30, 40, 50 and 80) having Variform® or Varimax piezo-ceramic fast tool servo attachment from Precitech, Inc.

Preferably, contact lenses are molded from contact lens molds including molding surfaces that replicate the contact lens surfaces when a lens is cast in the molds. For example, an optical cutting tool with a numerically controlled lathe may be used to form a metallic optical tool incorporating the features of the anterior surface of a contact lens of the invention. The tool is then used to make anterior surface molds that are then used, in conjunction with posterior surface molds, to form the lens of the invention using a suitable liquid lens-forming material placed between the molds followed by compression and curing of the lens-forming material.

Preferably, a contact lens of the invention or the optical tool to be used for making the same is fabricated by using a numerically controlled lathe, for example, such as Optoform® ultra-precision lathes (models 30, 40, 50 and 80) having Variform®) or Varimax piezo-ceramic fast tool servo attachment from Precitech, Inc, according to a method described in a co-pending U.S. Patent Application of CibaVision, entitled Method for Manufacturing a contact lens, (U.S. Ser. No. 60/398,495, filed on Jul. 24, 2002), herein incorporated by reference in its entirety.

As an illustrative example, production of a translating contact lens having a ramped ridge zone having a latitudinal ridge is created via the following process. First, a user defines a set of parameters, such as a surface tolerance, a concentricity tolerance, orientation of the lens design, the number of semi-diameter spokes to be generated for each of the anterior and posterior surfaces, creating zero point at 0,0, orientation of Z-axis, and type of lens surface (concave or convex surface) to be converted into a geometry. A "surface tolerance" refers to the allowed position-deviation of a projected point from an ideal position on a surface of a lens design. The deviation can be in the direction either parallel or perpendicular to the central axis of a lens design. A "concentricity tolerance" refers to the allowed deviation of a point from a given arc. A "semi-diameter spoke" refers to a curve radiating outwardly from the central axis and is perpendicular to the central axis and projected onto the surface. "Evenly-spaced semi-diameter spokes" means that all semi-diameter spokes radiate outwardly from the central axis and separate from each other by one equal angle. A "point spacing" refers to a distance between two points along the semi-diameter spoke.

Second, a user determines the point density to be projected onto the surface of the lens design (for example, the anterior surface) along each of the number of evenly-spaced semi-diameter spokes in a direction parallel to the central axis. A semi-diameter spoke at an azimuthal angle corresponds to the feature that deviates most from the base conic surface, and is selected as the semi-diameter probing spoke. Evenly-spaced points are projected along the semi-diameter probing spoke, in which each pairs of points are separating by a point spacing of typically 10 microns. Then all of the projected points are divided into a series of groups, with each group composed of three consecutive points, a first point, a middle point, and a third point. Each of the points can belong to either one group or two groups. One group is analyzed at a time from the central axis to the edge, or from the edge to the central axis, from the curvature of the surface at the middle point of the group by comparing a distance between the middle point and a line linking the first point and the third point of the corresponding group with the predetermined surface tolerance. If the distance between the middle point and the line linking the first and third points of the group is larger than the predetermined surface tolerance, the curvature of the surface at that point is sharp and an additional point is projected between the first and the middle points in that group. The point spacing between the first and additional points is equal to point spacing between the additional and middle points. After adding an additional point, all of the points included the newly added point is regrouped again and the curvature of the surface at the middle point of each of the series of groups is analyzed. Such iterative procedure is repeated until the distance between the middle point of each of the series of groups and the line linking the first and the third points of corresponding group along the probing spoke is equal to or less than the predetermined surface tolerance. In this manner, the number of the points to be projected onto the surface of the lens design along each of the desired number of evenly-spaced semi-diameter spokes and point spacing for a series of pairs of neighboring points are determined.

The above-determined number of points is then projected onto the anterior surface of the lens design along each of 24, 96 or 384 semi-diameter spokes, in the preferred embodiment. Other numbers of spokes are possible. For each of the semi-diameter spokes, a semi-meridian that is continuous in first derivative is generated. The semi-meridian includes a series of arcs and, optionally, straight lines wherein each arc is defined by fitting at least three consecutive points into a spherical mathematical function within a desired concentricity tolerance. Each of the straight lines is obtained by connecting at least three consecutive points. Preferably, the arc-fitting routine is started from the central axis to the edge. Similarly, conversion of the posterior surface of the lens design into geometry can be carried out according to the above-described procedure. After converting the lens design to geometry of a contact lens to be produced in a manufacturing system, a mini-file, or equivalent format, containing both the information for the header and the information about the geometry of the lens is generated. This mini-file also contains a zero semi-meridian that is based on the average height of each of the other meridians at each of radial locations and that gives the Variform or Varimax a zero position on which it can base its oscillation calculations. In this mini-file, all semi-meridians have the same number of zones. This is accomplished by copying the last zone of a semi-meridian for a number of times to equalize the numbers of zones for all meridians. After the mini-file is completed, it is loaded into an Optoform® ultra-precision lathe (models 30, 40, 50 or 80) having Variform® piezoceramic fast tool servo attachment and run to produce a translating contact lens.

The present invention also provides a method of manufacturing a pair of multifocal contact lenses, the method including the steps of designing a first contact lens and a second contact lens. Each of the first and second lenses comprises an anterior surface and an opposite posterior surface. The anterior surface of each lens includes a vertical meridian and horizontal meridian, and a central optical zone. The central optical zone of each lens has a superior optical zone, an inferior optical zone, and an optical blending zone, wherein the optical blending zone has a surface that ensures a smooth surface transition from the superior optical zone to the inferior optical zone and that allows the superior and inferior optical zones independently of each other to be designed and optimized so that ghost images or blur from the superior and inferior optical zones is minimized or eliminated. The superior optical zone of the first lens is for distance vision correction and the inferior zone of the first lens is for intermediate or near vision correction. The superior optical zone of the second lens is for distance or intermediate vision correction and the inferior zone of the second lens is for intermediate or near vision correction. Preferably, the vision correction of the inferior zone of the first lens, whether intermediate or near correction, will be set by the wearer's subjective preference and predominant daily activities.

All preferred design features of a contact lens of the invention described above can be incorporated in the manufacturing method of the invention.

The manufacturing method of the invention preferably further comprises a step of producing a contact lens by a manufacturing means as described above. Design of the anterior surface can also be performed according to information for vision correction for an eye 30 of a potential lens wearer.

While the foregoing disclosure shows illustrative embodiments of the invention, it should be noted that various changes and modifications could be made herein without departing from the scope of the invention as defined by the appended claims. Furthermore, although elements of the invention may be described or claimed in the singular, the plural is contemplated unless limitation to the singular is explicitly stated.

What is claimed is:

1. A pair of multifocal contact lenses, a first translating contact lens and a second translating contact lens, wherein each of the first and second lenses comprises an anterior surface and an opposite posterior surface, wherein the anterior surface of each lens includes a vertical meridian and horizontal meridian, and a central optical zone, wherein the central optical zone of each lens has a superior optical zone, an inferior optical zone, and an optical blending zone, wherein the optical blending zone has a surface that ensures a smooth surface transition from the superior optical zone to the inferior optical zone and that allows the superior and inferior optical zones independently of each other to be designed and optimized so that ghost images or blur from the superior and inferior optical zones is minimized or eliminated, wherein the superior optical zone of the first lens is for distance vision correction and the inferior zone of the first lens is for intermediate or near vision correction, wherein the superior optical zone of the second lens is for distance or intermediate vision correction and the inferior zone of the second lens is for intermediate or near vision correction, wherein the apex of the superior optical zone coincides with the center of the central optical zone, wherein the vertex center of the inferior optical zone is located at the intersection point of the vertical meridian or a line which is parallel to the vertical meridian and passes through the center of the central optical zone with its boundary line with the optical blending zone, wherein the width of the optical blending zone is about 0.1 mm or less at the center, and wherein a first line passing through the vertex center of the inferior optical zone and the center of curvature at the vertex center of the inferior optical zone intersects a second line passing through the apex of the superior optical zone and the center of curvature at the apex of the posterior surface, wherein the intersection point of the first line with the second line is within 2 mm or less of the center of curvature at the apex of the base optical surface.

2. The pair of multifocal contact lenses of claim 1, wherein the optical blending zone has a mirror symmetry with respect to a plane cutting through the vertical meridian or a line parallel to the vertical meridian and passing through the center of the central optical zone, wherein the surface of the optical blending zone has a localized curvature or optical power much higher than either of the first and second optical zones so that axial light will refract light from the macular region of the eye of the wearer.

3. The pair of multifocal contact lenses of claim 2, wherein the superior zones of the first and second lenses independently of each other have a manifest corrective refractive power for distance vision correction of one of the two eyes of a wear.

4. The pair of multifocal contact lenses of claim 3, wherein the inferior optical zone of the first lens has a near optical power for near vision correction while the inferior optical zone of the second lens has an intermediate optical power for intermediate vision correction, wherein the near optical power includes a first ADD value and the intermediate optical power includes a second ADD value, and wherein the second ADD value is between 25% and 75% of the first ADD value.

5. The pair of multifocal contact lenses of claim 4, wherein the second ADD value is from 0.5 to 1.5 diopters, and wherein the first ADD value is from 1.5 to 3.0 diopters.

6. The pair of multifocal contact lenses of claim 4, wherein the size ratio of the superior optical zone to the inferior optical zone for the first lens is about 1.6 or larger, and wherein the size ratio of the superior optical zone to the inferior optical zone for the second lens is about 1.5 or smaller.

7. The pair of multifocal contact lenses of claim 6, wherein for the first lens the distance from the apex of the superior optical zone to the intersection point of the vertical meridian or a line which is parallel to the vertical meridian and passes through the center of the central optical zone with the upper boundary line of the inferior optical zone with the optical blending zone is from 0.6 to 1.5 mm, and wherein for the second lens the distance from the apex of the superior optical zone to the intersection point of the vertical meridian or a line which is parallel to the vertical meridian and passes through the center of the central optical zone with the upper boundary line of the inferior optical zone with the optical blending zone is less than about 0.7 mm.

8. The pair of multifocal contact lenses of claim 2, wherein the superior zone of the first lens has a manifest corrective refractive power for distance vision correction of one of the two eyes of a wear, wherein the superior zone of the second lens has a first intermediate optical power for intermediate vision correction.

9. The pair of multifocal contact lenses of claim 8, wherein the inferior zones of the first and second lenses have a near optical power for near vision correction.

10. The pair of multifocal contact lenses of claim 9, wherein for both the first and the second lenses the size ratio of the superior optical zone to the inferior optical zone for the first lens is about 1.6 or larger.

11. The pair of multifocal contact lenses of claim 10, wherein the near optical power includes a first ADD value and the first intermediate optical power includes a second ADD value, and wherein the second ADD value is between 25% and 75% of the first ADD value.

12. The pair of multifocal contact lenses of claim 8, wherein the inferior optical zones of the first lens has a second intermediate optical power for intermediate vision correction and the inferior optical zone of the second lens has a near optical power for near vision correction.

13. The pair of multifocal contact lenses of claim 12, wherein the near optical power includes a first ADD value, wherein the first intermediate optical power includes a second ADD value, wherein the second intermediate optical power includes a third ADD value, and wherein the second ADD value and the third ADD value independently of each other is between 25% and 75% of the first ADD value.

14. The pair of multifocal contact lenses of claim 13, wherein for the second lens the size ratio of the superior optical zone to the inferior optical zone is about 1.5 or smaller, and wherein for the first lens the size ratio of the superior optical zone to the inferior optical zone for the second lens is about 1.6 or larger.

15. The pair of multifocal contact lenses of claim 14, wherein for the second lens the distance from the apex of the superior optical zone to the intersection point of the vertical meridian or a line which is parallel to the vertical meridian and passes through the center of the central optical zone with the upper boundary line of the inferior optical zone with the optical blending zone is from 0.6 to 1.5 mm, and wherein for the first lens the distance from the apex of the superior optical zone to the intersection point of the vertical meridian or a line which is parallel to the vertical meridian and passes through the center of the central optical zone with the upper boundary line of the inferior optical zone with the optical blending zone is less than about 0.7 mm.

16. The pair of multifocal contact lenses of claim 1, wherein each lens includes mechanical features to maintain positional and rotational stability of the lens on an eye.

17. The pair of multifocal contact lenses of claim 16, wherein the mechanical features are selected from the group consisting of: a prism ballast that uses a varying thickness profile to control the lens orientation; a faceted surface in which parts of the lens geometry is removed to control the lens orientation; a ridge feature which orients the lens by interacting with the eyelid; double slab-off features which have a top slab-off zone and a bottom slab-off zone zones to maintain the lens orientation on the eye; and non-prism ballast features in a peripheral zone of the lens, the peripheral zone surrounding the optical zone of the lens.

18. The pair of multifocal contact lenses of claim 1, wherein the anterior surface of each lens further includes a peripheral zone, an edge zone, a first blending zone extending outwardly from the central optical zone to the peripheral zone and providing a continuous transition from the central optical zone to the peripheral zone, a second blending zone extending outwardly from the peripheral zone to the edge zone and providing a continuous transition from the peripheral zone to the edge zone, wherein the anterior surface has a mirror symmetry with respect to the vertical meridian plane and is continuous at least in first derivative, wherein each lens is weighed at its lower half portion by varying lens thickness within the peripheral zone and second blending zone to cause it to come to an equilibrium position on an eye, and wherein each lens has a lens thickness profile characterized by that the lens thickness, in a sector bounded by two sector-bounding semi-meridians at about 35 degrees or larger relative to the lower portion of the vertical meridian and by a portion of the edge included between the two sector-bounding semi-meridians, increases gradually from the inner boundary of the peripheral zone along each semi-meridian until reaching a lens thickness maximum and then decreases.

19. The pair of multifocal contact lenses of claim 18, wherein the lens thickness profile is further characterized by that: (1) the lens thickness, along the upper portion of the vertical meridian, of each lens in the peripheral zone remains substantially constant or increases gradually from the outer boundary of the peripheral zone to the inner boundary of the peripheral zone in a manner that the difference between the values of lens thickness at two intersection points of the upper portion of the vertical meridian with the outer and inner boundaries of the peripheral zone is less than 50%; and/or (2) the lens thickness, along the lower portion of the vertical meridian, of the contact lens in the peripheral zone increases gradually from the inner boundary of the peripheral zone to the outer boundary of the peripheral zone in a manner that the difference between the values of lens thickness at two intersection points of the lower portion of the vertical meridian with the inner and outer boundaries of the peripheral zone is from about 15% to about 65%.

20. The pair of multifocal contact lenses of claim 1, wherein the superior optical zone of at least one of the first and second lenses includes a vertically oriented coma-like aberration that is more myopic in the inferior sections of the superior optical zone.

21. The pair of multifocal contact lenses of claim 1, wherein the central optical zone of at least one of the first and second lenses has a progressive power zone between the superior and inferior zones.

22. A method for manufacturing a pair of multifocal contact lenses, the method including the steps of designing a first contact lens and a second contact lens, wherein each of the first and second lenses comprises an anterior surface and an opposite posterior surface, wherein the anterior surface of each lens includes a vertical meridian and horizontal meridian, and a central optical zone, wherein the central optical zone of each lens has a superior optical zone, an inferior optical zone, and an optical blending zone, wherein the optical blending zone has a surface that ensures a smooth surface transition from the superior optical zone to the inferior optical zone and that allows the superior and inferior optical zones independently of each other to be designed and optimized so that ghost images or blur from the superior and inferior optical zones is minimized or eliminated, wherein the superior optical zone of the first lens is for distance vision correction and the inferior zone of the first lens is for intermediate or near vision correction wherein the superior optical zone of the second lens is for distance or intermediate vision correction and the inferior zone of the second lens is for intermediate or near vision correction, wherein the apex of the superior optical zone coincides with the center of the central optical zone, wherein the vertex center of the inferior optical zone is located at the intersection point of the vertical meridian or a line which is parallel to the vertical meridian and passes through the center of the central optical zone with its boundary line with the optical blending zone, wherein the width of the optical blending zone is about 0.1 mm or less at the center, and wherein a first line passing through the vertex center of the inferior optical zone and the center of curvature at the vertex center of the inferior optical zone intersects a second line passing through the apex of the superior optical zone and the center of curvature at the apex of the posterior surface, wherein the intersection point of the first line with the second line is within 2 mm or less of the center of curvature at the apex of the base optical surface.

23. The method of claim 22, further comprising the steps of producing the ophthalmic lens by a manufacturing means.

24. The method of claim 23, wherein the manufacturing means is a computer-controllable manufacturing device.

25. The method of claim 24, wherein the computer controllable manufacturing device is a numerically controlled lathe.

* * * * *